United States Patent [19]

Lawson

[11] 4,399,286

[45] Aug. 16, 1983

[54] ANTIARRHYTHMIC PHENETHYLPIPERIDINE COMPOUNDS

[75] Inventor: John E. Lawson, Evansville, Ind.

[73] Assignee: Mead Johnson & Company, Evansville, Ind.

[21] Appl. No.: 283,710

[22] Filed: Jul. 16, 1981

[51] Int. Cl.³ ........................................... C07D 211/28
[52] U.S. Cl. ..................................... 546/231; 424/267
[58] Field of Search ........................................ 546/231

[56] References Cited

U.S. PATENT DOCUMENTS

| | | | |
|---|---|---|---|
| 3,852,339 | 12/1974 | Krapto | 424/267 |
| 3,931,195 | 1/1976 | Dykstra et al. | 546/231 |
| 4,000,143 | 12/1976 | Dykstra et al. | 546/231 |
| 4,007,181 | 2/1977 | Ducharme et al. | 546/231 |
| 4,064,254 | 12/1977 | Dykstra et al. | 546/231 |
| 4,066,695 | 1/1978 | Cohen et al. | 546/231 |
| 4,071,524 | 1/1978 | Banitt | 546/231 |
| 4,073,790 | 2/1978 | Archibald et al. | 424/267 |

FOREIGN PATENT DOCUMENTS 1290365 9/1972 United Kingdom .
1290366 9/1972 United Kingdom .

OTHER PUBLICATIONS

Burger Medicinal Chemistry, Third Edition, Part 1, pp. 64 to 79.
Hansch et al., Journal of Medicinal Chemistry 1973, vol. 16, No. 11, pp. 1207–1216 and vol. 19, No. 1, pp. 1–5.
Durant et al., Journal of Medicinal Chem. 1977, vol. 20, No. 7, pp. 901–906.
Chronicles of Drug Discovery, vol. 1, 1982, John Wiley & Sons, Inc., pp. 1–37.
Dykstra et al., Jour. of Medicinal Chem. 16, 1015 (1973).
Byrne et al., The Jour. of Pharmacology and Experimental Therapeutics, vol. 200, No. 1, p. 147, 1977.

*Primary Examiner*—Jane T. Fan
*Attorney, Agent, or Firm*—Richard P. Ryan; Robert H. Uloth

[57] ABSTRACT

2-Phenethylpiperidines bearing urea, thiourea, and amidine substituents in the ortho-position of the phenethyl moiety have been synthesized and demonstrate useful antiarrhythmic properties. These novel compounds are prepared by reaction of appropriately substituted o-amino-phenethylpiperidines with appropriately substituted phenyl isothiocyanates, phenyl isocyanates, or phenyl imino esters.

2 Claims, No Drawings

ANTIARRHYTHMIC PHENETHYLPIPERIDINE COMPOUNDS

FIELD OF THE INVENTION

The subject compounds of the invention are heterocyclic carbon compounds of the piperidine series having an additional ring and having nitrogen attached indirectly to the piperidine ring by non-ionic bonding (Class 546, Subclass 229).

BACKGROUND OF THE INVENTION

The present invention concerns certain 2-phenethylpiperidines bearing either urea, thiourea, or amidine substituents in the ortho-position of the phenethylamine phenyl ring. This invention particularly relates to these compounds and their acid addition salts with respect to their antiarrhythmic properties.

A related series of antiarrhythmic 2-phenethylpiperidines bearing amide substituents in the ortho-position of the phenyl ring has been previously described. One embodiment of that series is an antiarrhythmic agent known as encainide which is currently undergoing clinical evaluation. Encainide hydrochloride is also referred to in the literture as MJ 9067 (USAN and the USP Dictionary of Drug Names 1980, p. 122, United States Pharmacopeial Convention, Inc., 12601 Twinbrook Parkway, Rockville, MD 20852, Library of Congress Catalog Card No. 72-88571). Encainide has the following structural formula (1)

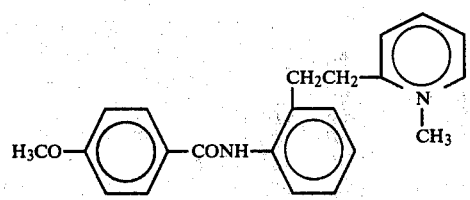

The following publications describe the chemical synthesis of encainide and closely related compounds and its antiarrhythmic properties in animals.

Dykstra, S. J., et al., *J. Med. Chem.*, 16, 1015–1020 (1973).

S. J. Dykstra and J. L. Minielli, U.S. Pat. No. 3,931,195 patented Jan. 6, 1976; U.S. Pat. No. 4,000,143 patented Dec. 28, 1978; U.S. Pat. No. 4,064,254 patented Dec. 20, 1977.

Byrne, J. E., et al., *J. Pharmacology and Experimental Therapeutics*, 200, 147–154 (1977).

Prior art related to the present invention is described in E. R. Squibb & Sons, Inc., British Specification Nos. 1,290,365 and 1,290,366 (divisionals) published Sept. 27, 1972.

These two British patents disclose substituted ureas with antiarrhythmic properties having the generic formula (2)

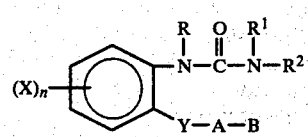

Although some of the urea compounds of the instant invention read on this generic formula, none of them is exemplified or shown as a specific embodiment in the British specifications.

A related reference is Krapcho, J., U.S. Pat. No. 3,852,339 issued Dec. 3, 1974. This patent discloses aminoalkoxyphenylurea derivatives with antiarrhythmic properties. These compounds have general structure (3)

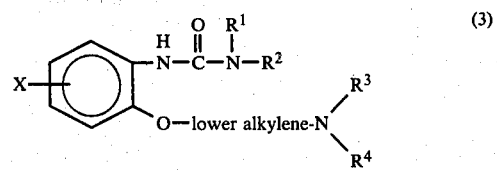

The incorporation of an ether oxygen atom in the alkyl chain of these compounds additionally distinguishes them from the instant urea compounds.

The piperidino ureas and thioureas (4)

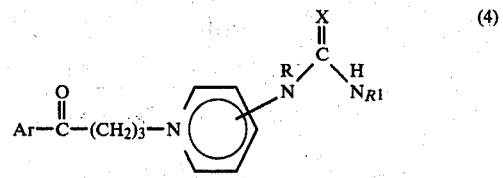

described in Archibald, J. L. and Jackson, J. L., U.S. Pat. No. 4,073,790 issued Feb. 14, 1978 are disclosed as having antihypertensive utility. They bear some of the same structural elements as the presently claimed substances, but are otherwise dissimilar.

The structures of encainide and a number of analogs thereof, described in the foregoing publications and patents, differ from the compounds comprising the instant invention in the nature of the phenethyl moiety's ortho substituent. Encainide and its related analogs have o-amido functions whereas the subject compounds of this application have o-urea, -thiourea, and -amidine substituents thereon.

SUMMARY OF THE INVENTION

This invention is concerned with a new series of antiarrhythmic compounds characterized by the following general structure of Formula I and the non-toxic pharmaceutically acceptable acid addition salts thereof.

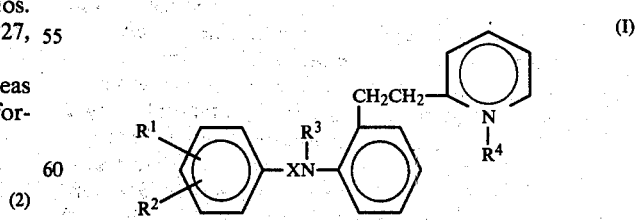

In the foregoing formula: $R^1$ is hydrogen, halogen, lower (meaning 1 to 4 carbon atoms inclusive) alkyl, lower alkoxy or lower alkylthio; $R^2$ is hydrogen, hydroxy, or methoxy; $R^3$ is hydrogen or lower alkyl; $R^4$ is hydrogen or lower alkyl; and X is the divalent group

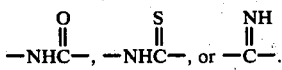

DETAILED DESCRIPTION OF THE INVENTION

Preparation of the compounds of the instant invention can be accomplished by the unitary process depicted below.

pyridine, and the like are generally operable. The desired products are isolated and purified using standard methods familiar to a practitioner skilled in the art. Such a practitioner would also appreciate that the amidine structure

for Formula I compounds is capable of existence in tautomeric form when $R^3$ is hydrogen.

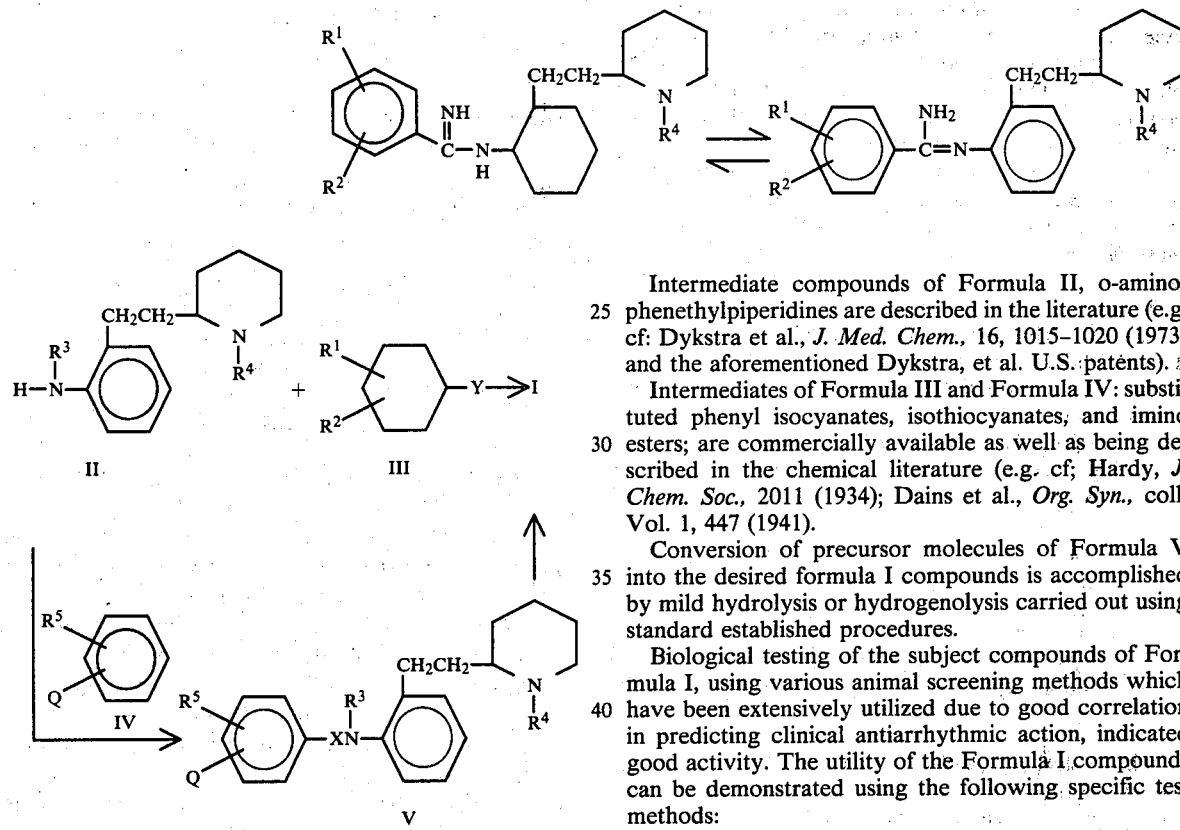

In this scheme, $R^1$, $R^2$, $R^3$, and $R^4$ have the same meanings as previously assigned to Formula I. Q is a hydroxy group synthon, a group capable of facile conversion to —OH, e.g. benzyloxy or acetoxy. $R^5$ is independently selected from Q or the group defined by $R^1$. The symbol Y refers to a reactive grouping on III or IV, susceptible to attack by the o-amino moiety of compound II. As such, Y can be an isocyanate, isothiocyanate, or iminoester group. The process is carried out under conditions suitable for amine addition or condensation with isocyanates, isothiocyanates, or imino esters. The process specifically involves mixing approximately stoichiometric quantities of an appropriately substituted intermediate o-aminophenethylpiperidine of Formula II, dissolved in a suitable non-reactive organic liquid; with an appropriate intermediate compound of Formula III and then stirring these reactants for about 12 to 24 hours at temperatures which can range from ambient room temperature to reflux of the organic liquid medium. Benzene, toluene, and xylene are preferred liquids for carrying out the process although other solvents commonly employed in reactions of this type may be used, e.g. chloroform, dichloroethane, ethyl acetate, Intermediate compounds of Formula II, o-aminophenethylpiperidines are described in the literature (e.g. cf: Dykstra et al., *J. Med. Chem.*, 16, 1015–1020 (1973) and the aforementioned Dykstra, et al. U.S. patents).

Intermediates of Formula III and Formula IV: substituted phenyl isocyanates, isothiocyanates, and imino esters; are commercially available as well as being described in the chemical literature (e.g. cf; Hardy, *J. Chem. Soc.*, 2011 (1934); Dains et al., *Org. Syn.*, coll. Vol. 1, 447 (1941).

Conversion of precursor molecules of Formula V into the desired formula I compounds is accomplished by mild hydrolysis or hydrogenolysis carried out using standard established procedures.

Biological testing of the subject compounds of Formula I, using various animal screening methods which have been extensively utilized due to good correlation in predicting clinical antiarrhythmic action, indicated good activity. The utility of the Formula I compounds can be demonstrated using the following specific test methods:

1. In the dog, aconitine-induced arrhythmia is prevented by parenteral administration of the piperidines of Formula I according to the following in vivo test. The chest of an anesthetized dog is opened in the midline and the right and left ventrical appendages exposed through small slits in the pericardium. Bipolar recording electrodes are fixed to the atrial surfaces and a 4×4 mm piece of clean gauze was fixed to the surface of the right auricular appendage. Control recordings are made of various heart functions including femoral arterial blood pressure and right and left atrial electrograms. Atrial arrythmia is induced by placing three to five drops of solution of aconitine on the gauze affixed to the right atrium. An irregular, rapid atrial rate is produced within one minute. Throughout the experiment, fresh aconitine (two to three drops) is placed on the gauze at ten minute intervals. The test compound is administered intravenously five minutes after the initial establishment of the arrhythmia and its infusion contained at a slow rate until an effective dose which reestablishes normal rhythm of the heart is obtained.

Intravenous administration of 2 to 4 mg/kg of 2-[2-(1-methyl-2-piperidinyl)ethyl]thiocarbanilide, a representative compound (Example 9) of the present invention, effectively restores normal cardiac rhythm to aconitine-induced arrhythmia in the dog.

2. In the mouse, another in vivo test involves the inhibition of chloroform-induced arrhythmia according to the method of J. W. Lawson, *Journal of Pharmacology and Experimental Therapeutics*, 160, 22 (1968). Intraperitoneal administration of 2-[2-(1-methyl-2-piperidinyl)ethyl]carbanilide (Example 1) and the 4'-methoxy analog (Example 2) representative compounds of the present invention, to the mouse prevent chloroform-induced arrhythmia at an $ED_{50}$ of 23 mg/kg and 46 mg/kg, respectively.

3. An in vitro test which demonstrates the antiarrhythmic effects of Formula I employs the rabbit atrium. In this test, the left atrium is placed in Chenoweth's solution warmed to 30° C. and irrigated with 95% oxygen:5% carbon dioxide. The lower end of the atrium is attached to a small hook fixed in the bath and the upper end is connected to a transducer to record contractile activity. The atrium is electrically stimulated at a basic rate of 30/minute by employing square wave pulses of 10 millisecond duration at 1.2 to 1.5 times threshold voltage. A test compound is introduced into the bath and the test repeated after a five minute interval. A dose-response relationship is obtained with additional doses of the test compound. The potency of a test compound can be expressed as the effective concentration which reduces to 50% the maximal increase in the measure of the steady state refractory period of the atrium. This value is designated the $EC_{50}$. The $EC_{50}$ values of some representative compounds of the present invention are shown below.

| Cmpd. Product of; | X | $EC_{50}$ (μg/ml) |
|---|---|---|
| Ex. 1 | $-NH\overset{O}{\underset{\|}{C}}-$ | 1.5 |
| Ex. 2 | $-NH\overset{O}{\underset{\|}{C}}-$ | 29 |
| Ex. 9 | $-NH\overset{S}{\underset{\|}{C}}-$ | 5.9 |
| Ex. 15 | $-\overset{NH}{\underset{\|}{C}}-$ | 10 |

Accordingly, another embodiment of the present invention concerns a process for eliciting an antiarrhythmic effect in a mammal which comprises administering to said mammal, either orally or parenterally, a non-toxic effective antiarrhythmic dose of from 0.1 to 50 mg/kg of body weight of said mammal of a Formula I compound or a non-toxic pharmaceutically acceptable acid addition salt thereof. It is to be understood that as used herein, the term "non-toxic pharmaceutically acceptable acid addition salt" refers to a combination of compounds of the present invention with relatively non-toxic inorganic or organic acids. Illustrative of suitable acids which may be used are sulfuric, phosphoric, hydrochloric, hydrobromic, hydroiodic, sulfamic, methanesulfonic, benzenesulfonic, para-toluenesulfonic, acetic, lactic, succinic, maleic, mucic, tartaric, citric, gluconic, benzoic, cinnamic, isethionic. and related acids. It will also be apparent to those skilled in the art that the compounds of Formula I exist in at least one racemic stereoisomeric form since they contain at least one asymmetric carbon atom (the two position of the piperidine ring). Such racemic modifications can be separated into the individual optical isomers on the basis of physio-chemical differences such as solubility; for example, by fractional crystallization of the base as acid addition salts using optically active acids thereof, or by chromatography. Optically active stereoisomers can be obtained by resolution methods well known to the art.

When the Formula I compounds of this invention are employed as antiarrhythmic agents they may be administered to mammals alone or in combination with a pharmaceutically acceptable carrier. The proportion of the pharmaceutical carrier is determined by the solubility and chemical nature of the compound and chosen route of administration in standard pharmaceutical practice. For example, hey may be administered orally in form of tablets, coated tablets or capsules containing such excipients as starch, milk, sugar, certain types of clay, gelatin, stearic acid or salts thereof, e.g. magnesium or calcium stearate, talc, vegetable fats or oils, gums, glycols and other known excipients. They may also be administered orally in the form of solutions which may contain coloring, flavoring agents, or they may be injected parenterally, that is intramuscularly, intravenously, or subcutaneously. For parenteral administration, they may be used in the form of a sterile solution. Said pharmaceutical compositions are prepared by conventional methods.

A recommended dosage unit form comprises a pharmaceutical carrier and the therapeutically active compound in an amount sufficient to provide a non-toxic effective antiarrhythmic dose ranging from about 0.1 to 50 mg/kg of body weight of the mammal treated.

DESCRIPTION OF SPECIFIC EMBODIMENTS

The following examples are used to illustrate the present invention. As such, they are not to be construed as limiting the scope of the claims in any manner whatsoever.

EXAMPLE 1

2-[2-(1-Methyl-2-piperidinyl)ethyl]carbanilide

A solution consisting of 2-(ortho-aminophenethyl)-1-methylpiperidine (6.5 g; 0.03 mole) in 50 ml of benzene was stirred at room temperature. A solution of phenylisocyanate (3.3 ml; 0.03 mole) in 50 ml of benzene was added dropwise to the stirred aminophenethylpiperidine solution. After completion of the addition, stirring at room temperature was continued and a solid slowly precipitated. This reaction mixture was allowed to stand at room temperature overnight and was then filtered giving 8.6 g of white solid, m.p. 149°–153° C. Recrystallization from benzene afforded 6.1 g of pure product, m.p. 150°–151.5° C.

Anal. Calcd. for $C_{21}H_{27}N_3O$: C, 74.74; H, 8.07; N, 12.45. Found: C, 74.72; H, 8.13; N, 12.36.

NMR (CDCl$_3$); chemical shift (number protons, multiplicity)—1.50 (10,m); 2.31 (3,s); 2.70 (3,m); 6.70 (1,bs); 7.21 (8,m); 7.70 (1,m); 9.30 (1,bs).

IR (KBr): 700, 750, 1240, 1450, 1500, 1560, 1600, 1650, 2940, and 3320 cm$^{-1}$.

EXAMPLE 2

4'-Methoxy-2-[2-(1-methyl-2-piperidinyl)ethyl]carbanilide

A solution of para-methoxyphenylisocyanate (4.5 g; 0.03 mole) in 50 ml of benzene was added dropwise to a stirred solution of 6.5 g of the ortho-aminophenethyl-piperidine in 50 ml benzene as in Example 1. Filtration yielded 9.0 g of white solid, m.p. 159°–161° C. Recrystallization of the solid from approximately 250 ml ethyl acetate afforded 7.5 g of pure product, m.p. 161°–162° C.

Anal. Calcd. for $C_{22}H_{29}N_3O_2$: C, 71.90; H, 7.95; N, 11.44. Found: C, 71.99; H, 7.99; N, 11.47.

NMR (CDCl$_3$): 1.54 (10,m); 2.22 (3,s); 2.64 (3,m); 3.69 (3,s); 6.68 (3,m); 7.10 (5,m); 7.55 (1,m); 8.68 (1,bs).

IR (KBr): 750, 825, 1235, 1450, 1510, 1555, 1600, 1640, 2930, and 3300 cm$^{-1}$.

Similar Formula I carbanilides can be made (see Table 1) as illustrated above using the appropriate intermediates II and III.

Conversion to the Mucate Salt

Mucic acid (3.0 g; 0.015 mole) was added in small portions to a refluxing solution of the crude thiocarbanilide product in 100 ml of methanol. After completion of addition of the acid, the reaction mixture was chilled in an ice bath and unreacted mucic acid was removed by filtration. Upon standing the mucate salt crystallized from solution and was filtered, washed with additional cold methanol and air dried to give 8.7 g of crude solid. Recrystallization twice from methanol yielded 3.6 g of hydrated pure product, m.p. 120.5°–129.5° (bubbling).

Anal. Calcd. for $C_{21}H_{27}N_3S.\frac{1}{2}C_6H_{10}O_8.H_2O$: C, 60.48; H, 7.19; N, 8.82. Found: C, 60.41; H, 7.19; N, 8.75.

NMR (D$_2$O): 1.80 (8,m); 2.65 (2,m); 2.79 (3,s); 3.24 (3,m); 3.94 (1,s); 4.22 (1,s); 4.70 (HDO+5,s); 7.39 (9,m).

IR (KBr): 705, 760, 1320, 1450, 1500, 1535, 1600, 2955, 3270, and 3430 cm$^{-1}$.

Similar thiocarbanilides can be synthesized as illustrated above using appropriate II and III intermediates (see table 2).

TABLE 1

Additional Formula I Carbanilides

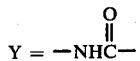

$Y = -NHC-$ (with O double bond)

| Example | R$^1$ | R$^2$ | R$^3$ | Reactants |
|---|---|---|---|---|
| 3 | 4-SCH$_3$ | H | CH$_3$ CH$_3$ | 2-(o-methylaminophenethyl)-1-methylpiperidine and 4-methylthiophenyl isocyanate |
| 4 | 2-Cl | H | H CH$_3$ | 2-(o-aminophenethyl)-1-methylpiperidine and 2-chlorophenyl isocyanate |
| 5 | 3-C$_3$H$_7$ | H | H CH$_3$ | 2-(o-aminophenethyl)-1-methylpiperidine and 3-propylphenyl isocyanate |
| 6 | 3-Br | H | CH$_3$ C$_2$H$_5$ | 2-(o-methylaminophenethyl)-1-ethylpiperidine and 3-bromophenyl isocyanate |
| 7 | 4-(t-butoxy) | H | H CH$_3$ | 2-(o-aminophenethyl)-1-methylpiperidine and 4-(t-butoxyphenyl)isocyanate |
| 8 | 4-OCH$_3$ | 3-OCH$_3$ | H CH$_3$ | 2-(o-aminophenethyl)-1-methylpiperidine and 3,4-dimethoxyphenyl isocyanate |

EXAMPLE 9

2-[2-(1-Methyl-2-piperidinyl)ethyl]thiocarbanilide

A solution of phenylisothiocyanate (3.0 ml; 0.033 mole) in 50 ml of benzene was added dropwise to a stirred solution of 6.5 g of the o-aminophenethylpiperidine in 50 ml benzene as in Example 1. Concentration in vacuo of the reaction solution yielded 10 g of product in the form of a visco yellow gum.

TABLE 2

Additional Formula I Thiocarbanilides $Y = -NHC-$ (with O double bond)

| Example | R$^1$ | R$^2$ | R$^3$ | R$^4$ | Reactants |
|---|---|---|---|---|---|
| 10 | H | 4-OCH$_3$ | H | CH$_3$ | 2-(o-aminophenethyl)-1-methylpiperidine and 4-methoxyphenyl isothiocyanate |
| 11 | 2-F | H | CH$_3$ | C$_3$H$_7$ | 2-(o-methylaminophenethyl)-1-propylpiperidine and 2-fluorophenyl isothiocyanate |
| 12 | 3-C$_2$H$_5$ | H | H | CH$_3$ | 2-(o-aminophenethyl)-1-methylpiperidine and 3-ethylphenyl isothiocyanate |
| 13 | 4-SCH$_3$ | H | C$_2$H$_5$ | H | 2-(o-ethylaminophenethyl)-piperidine and 4-methylthiophenyl isothiocyanate |
| 14 | 4-Cl | H | H | CH$_3$ | 2-(o-aminophenethyl)-1-methylpiperidine and 4-chlorophenyl isothiocyanate |

EXAMPLE 15

N-[2-[2-(1-Methyl-2-piperidinyl)ethyl]phenyl]-p-anisamidine

A solution consisting of 4-methoxybenzoic acid ethyl imino ester (8.2 g; 0.046 mole) and the o-aminophenethylpiperidine (8.0 g; 0.037 mole) in 100 ml of toluene was heated to reflux. A solution of acetic acid (2.2 g; 0.037 mole) in 50 ml toluene was added dropwise. After refluxing for an additional 4½ hours the reaction mixture was concentrated to dryness and the residue taken up in dilute HCl and washed with $Et_2O$. This acidic solution was made basic with 50% NaOH and extracted with benzene. The benzene extracts were combined, water-washed, and dried ($MgSO_4$), then concentrated to dryness. The resulting yellow oil was dissolved in 0.5 liter of isopropylether and allowed to stand overnight. Filtration yielded 9 g of crude product which was recrystallized from ethyl acetate to give 8.0 g product, m.p. 140.5°–141° C.

Anal. Calcd. for $C_{22}H_{29}N_3O$: C, 75.17; H, 8.32; N, 11.96. Found: C, 75.07; H, 8.39; N, 11.93.

NMR ($CDCl_3$): 1.64 (10,m); 2.18 (3,s); 2.62 (3,m); 3.79 (3,s); 4.65 (2,bs); 7.00 (6,m); 7.77 (2,m).

IR (KBr): 750, 840, 1255, 1380, 1520, 1575, 1600, 1630, 2780, 2940, 3320, and 3455 $cm^{-1}$.

Similar amidines can be made as illustrated above using the appropriate II and III intermediates (see Table 3).

TABLE 3

Additional Formula I Amidines $$Y = -\overset{NH}{\underset{}{\overset{\|}{C}}}-$$

| Example | $R^1$ | $R^2$ | $R^3$ | $R^4$ | Reactants |
|---|---|---|---|---|---|
| 16 | 4-Br | H | $CH_3$ | $C_2H_5$ | 2-(o-methylaminophenethyl)-1-ethylpiperidine and ethyl 4-bromobenzimidate |
| 17 | 3-Bu | H | H | $CH_3$ | 2-(o-aminophenethyl)-1-methylpiperidine and ethyl 3-butylbenzimidate |
| 18 | 4-OEt | H | H | $CH_3$ | 2-(o-aminophenethyl)-1-methylpiperidine and ethyl 4-ethoxybenzimidate |
| 19 | 3-SMe | H | $CH_3$ | $CH_3$ | 2-(o-methylaminophenethyl)-1-methylpiperidine and ethyl 3-methylthiobenzimidate |

The following examples illustrate formation of Formula V compounds (Table 4) and their conversion to hydroxy-group-containing compounds of Formula I. By appropriate selection of reactants, additional Formula V and hydroxy-containing Formula I compounds can be prepared.

TABLE 4

Formula V Compounds

| Example | $R^1$ | Q | $R^3$ | $R^4$ | X | Reactants |
|---|---|---|---|---|---|---|
| 20 | H | $4-O_2CCH_3$ | H | Me | $-NH\overset{O}{\overset{\|}{C}}-$ | 2-(o-aminophenethyl)-1-methyl-piperidine and 4-acetoxyphenyl isocyanate |
| 21 | $3-OCH_3$ | $4-O_2CCH_3$ | H | Me | $-NH\overset{O}{\overset{\|}{C}}-$ | 2-(o-aminophenethyl)-1-methyl-piperidine and 4-acetoxy-3-methoxyphenyl isocyanate |
| 22 | H | $4-O_2CCH_3$ | H | Me | $-NH\overset{S}{\overset{\|}{C}}-$ | 2-(o-aminophenethyl)-1-methyl-piperidine and 4-acetoxyphenyl isothiocyanate |
| 23 | $3-OCH_3$ | $4-O_2CCH_3$ | H | Me | $\overset{NH}{\overset{\|}{-C-}}$ | 2-(o-aminophenethyl)-1-methyl piperidine and ethyl 4-acetoxy-3-methoxybenzimidate |
| 24 | H | $4-O_2CCH_3$ | H | Me | $\overset{NH}{\overset{\|}{-C-}}$ | 2-(o-aminophenethyl)-1-methyl piperidine and ethyl 4-acetoxybenzimidate |
| 25 | $3-OCH_3$ | $4-OCH_2Ph$ | H | Me | $-NH\overset{S}{\overset{\|}{C}}-$ | 2-(o-aminophenethyl)-1-methyl-piperidine and 4-benzyloxy-3-methoxyphenyl isothiocyanate |

EXAMPLE 26

4'-Hydroxy-2-[2-(1-methyl-2-piperidinyl)ethyl]carbanilide

Suspend 4'-acetoxy-2-[2-(1-methyl-2-piperidinyl)ethyl]carbanilide (Example 20) in 1 N NaOH and stir until solution takes place. Adjust the pH of the aqueous solution of 9 with 6 N HCl. Extraction with $CHCl_3$ and concentration in vacuo of the extracts yields a crude material which is crystallized from alcohol.

EXAMPLE 27

4'-Hydroxy-3'-methoxy-2-[2-(1-methyl-2-piperidinyl)ethyl]thiocarbanilide

An alcoholic solution of 4'-benzyloxy-3'-methoxy-2-[2-(1-methyl-2-piperidinyl)ethyl]thiocarbanilide (Example 25) is catalytically hydrogenated using low pressure apparatus and 10% palladium on carbon catalyst at 50–60 psi until one equivalent of hydrogen is absorbed. The catalyst is removed by filtration and the filtrate concentrated in vacuo to give crude product which is converted to the mucate salt and purified by crystallization.

What is claimed is:

1. A compound selected from the group consisting of a compound having Formula (I)

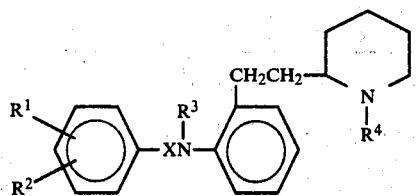 (I)

or a pharmaceutically acceptable salt thereof wherein $R^1$ is hydrogen, halogen, lower (meaning 1 to 4 carbon atoms inclusive) alkyl, lower alkoxy or lower alkylthio;

$R^2$ is hydrogen, hydroxy or methoxy;

$R^3$ and $R^4$ are independently selected from hydrogen or lower alkyl;

X is the divalent group

2. The compound of claim 1, N-[2-[2-(1-methyl-2-piperidinyl)ethyl]phenyl]-p-anisamidine or a pharmaceutically acceptable salt thereof.

* * * * *